US00PP33086P2

(12) United States Plant Patent
Olesen

(10) Patent No.: US PP33,086 P2
(45) Date of Patent: May 25, 2021

(54) MINIATURE ROSE PLANT NAMED 'POULPAR118'

(50) Latin Name: *Rosa hybrida*
Varietal Denomination: Poulpar118

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,995

(22) Filed: Sep. 3, 2020

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 121
See application file for complete search history.

*Primary Examiner* — Susan McCormick Ewoldt

(57) ABSTRACT

A new garden rose plant of the Miniature class which has abundant, pink flowers and attractive foliage. This new and distinct variety has shown to be uniform and stable in the resulting generations from asexual propagation.

3 Drawing Sheets

Botanical designation: *Rosa hybrida.*
Variety denomination: 'Poulpar118'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpar118', originated as a single seedling from the stated cross.

The new variety may be distinguished from its male pollen parent and female seed parent primarily by the following characteristics. The male pollen parent plant has light pink, Red Group 56C, flowers while the new variety has pink, Red-Purple Group 62B, flowers. The female seed parent plant has near white flowers while the new variety has pink, specifically Red-Purple Group 62B flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance.

This combination of qualities is not present in previously available commercial cultivars of this type, known to the inventor, and distinguish 'Poulpar118' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpar118' was selected in the spring of 2013 by the inventor as a single plant from the progeny of the aforementioned hybridization.

Asexual reproduction of 'Poulpar118' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpar118' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar118'.

Specifically illustrated in FIG. 1 of the drawings are flower petals and sepals detached showing reproductive flower parts of the flower, and flower bud.

Figure 1:
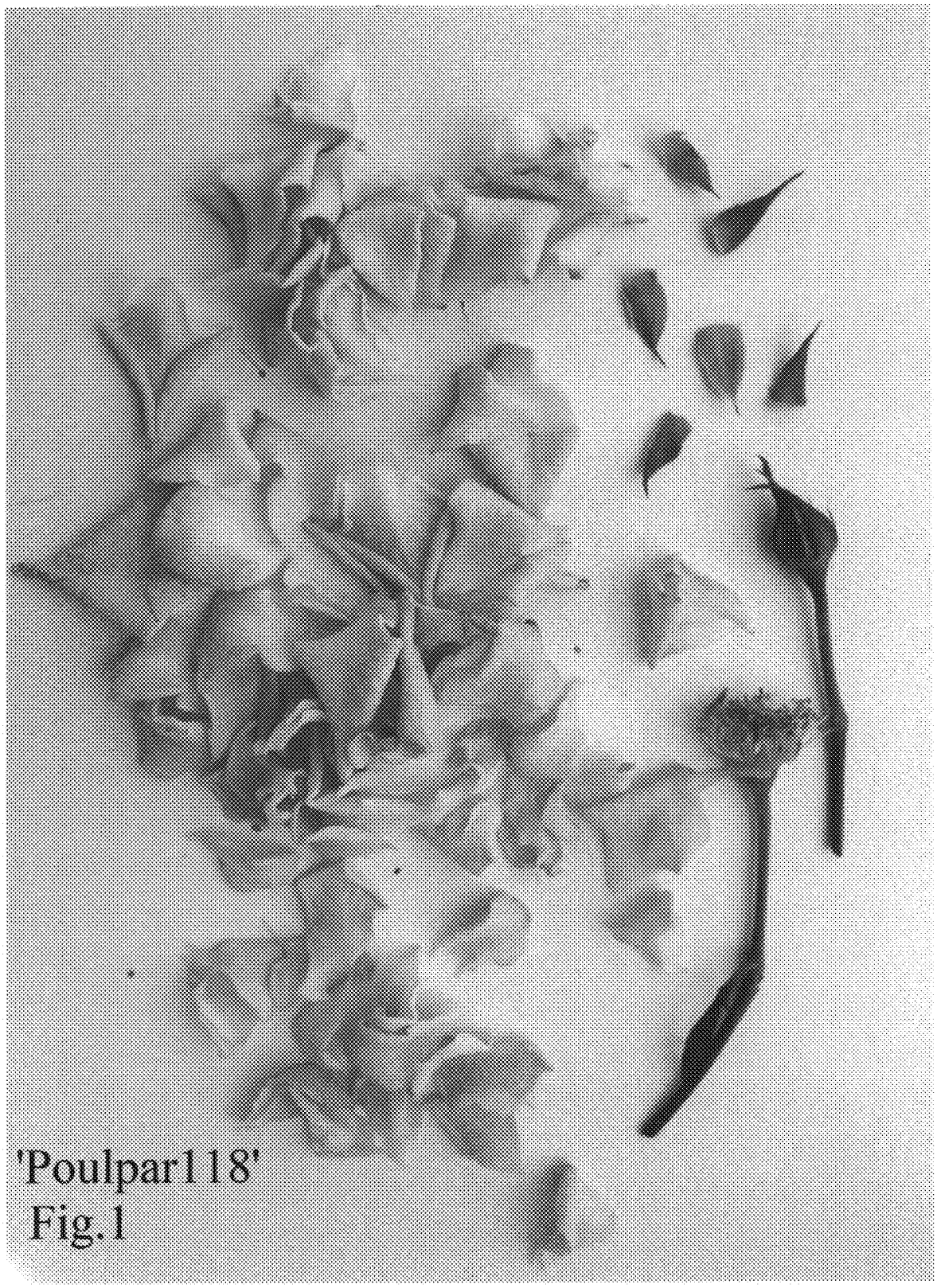
Figure 2:
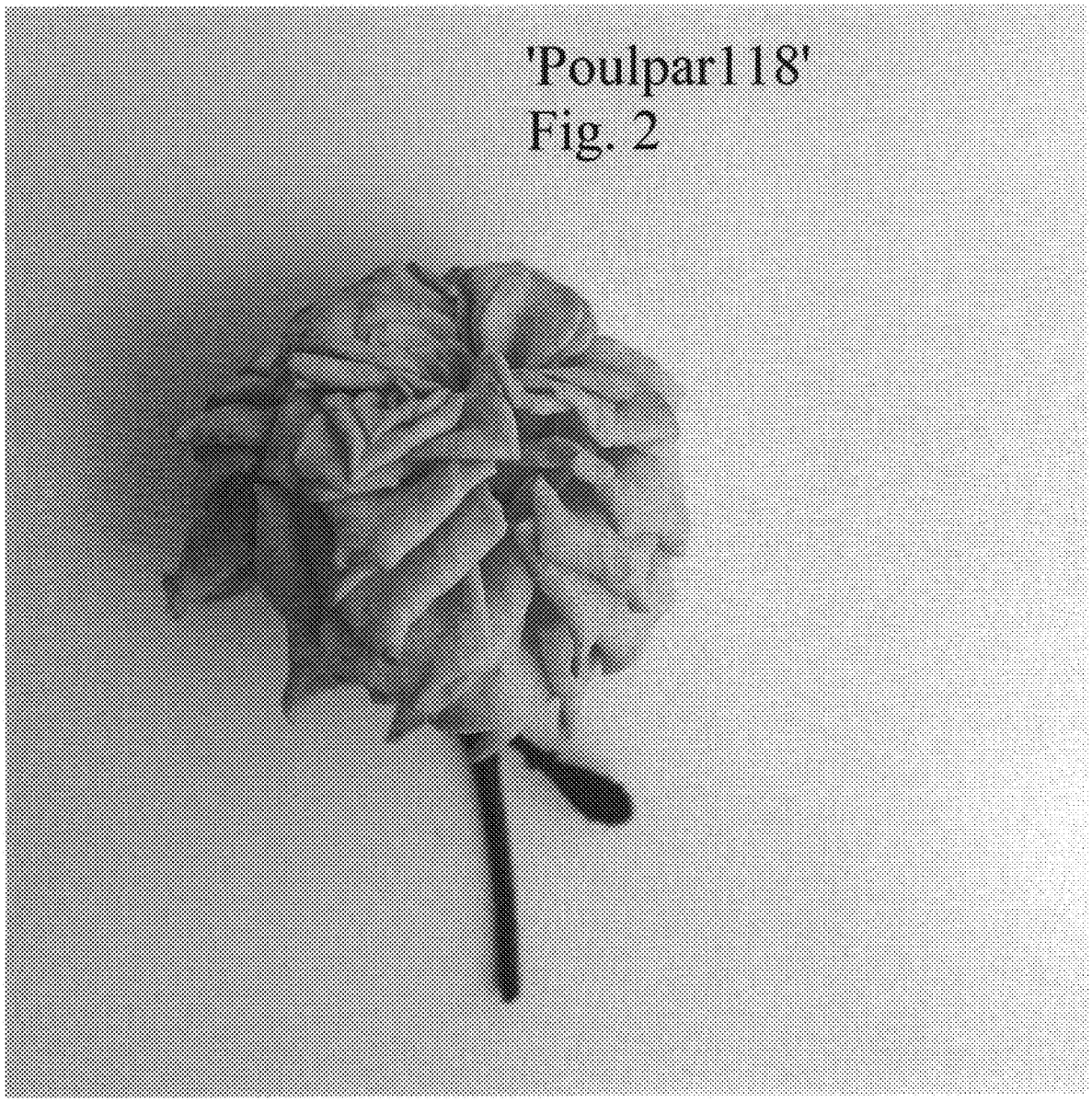

Specifically illustrated in FIG. 2 of the drawings are an open flower.

Figure 3:
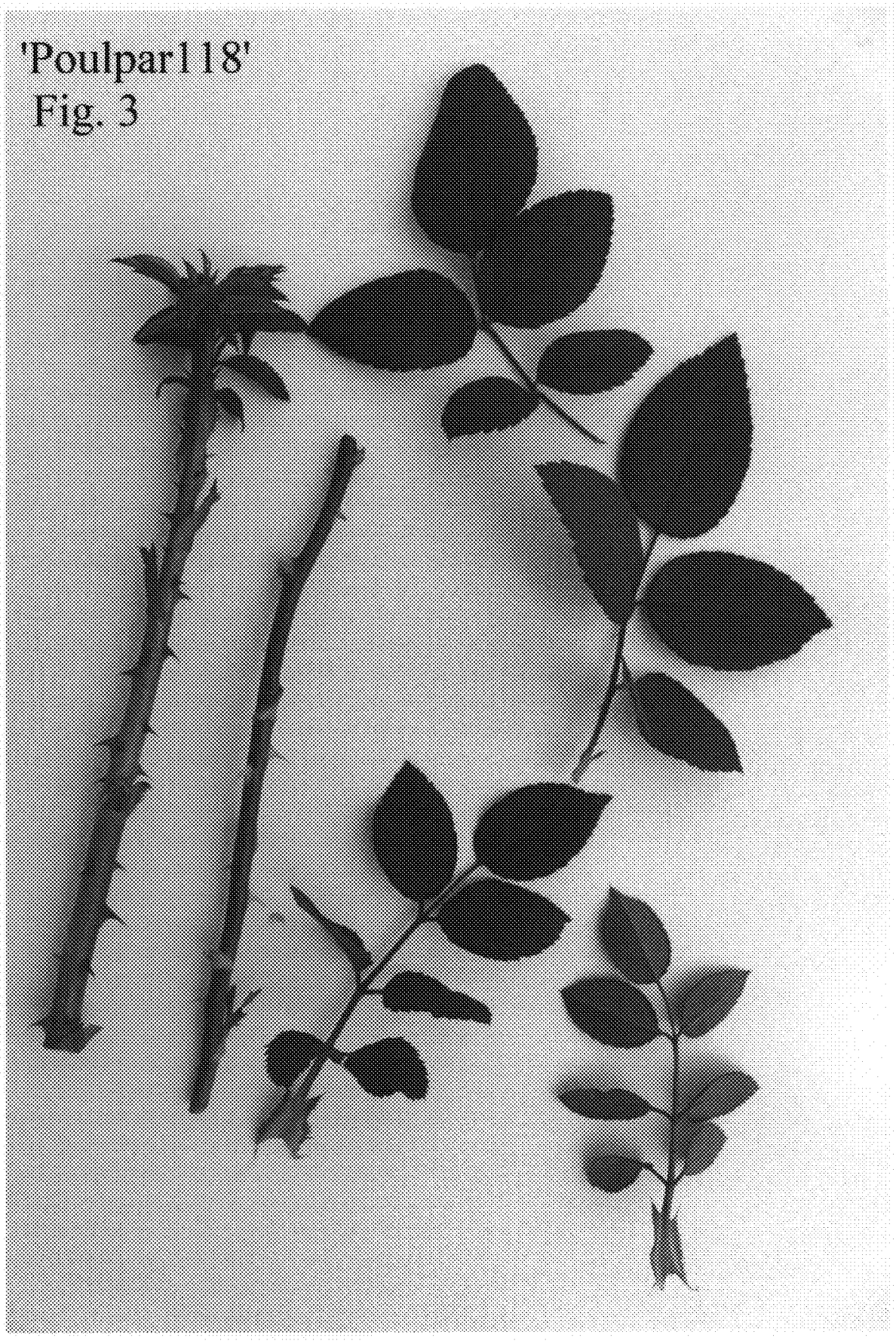

Specifically illustrated in FIG. 3 of the drawings are juvenile bare stem and mature bare stem, juvenile and mature leaves. Plants shown are 4 months old.

DETAILED DESCRIPTION OF THE VARIETY

The following is a description of 'Poulpar118', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulra024', U.S. Plant Pat. No. 15,017 are compared to 'Poulpar118' in Chart 1.

CHART 1

| 'Poulpar118' | 'Poulra024' | |
|---|---|---|
| Petal Count | 65 | 31 |
| Flower Diameter | 65 mm | 45 mm |
| General Tonality of Flower Color | Red-Purple Group 62B | Red Group 52C |

FLOWER AND FLOWER BUD

Blooming habit: Continuous.

Flower bud:

*Size*.—Upon opening, 25 mm in length from base of receptacle to end of bud. Bud diameter is 12 mm.

*Bud form*.—Ovoid.

*Sepal inner surface*.—Color: Yellow-Green Group 146D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—17 mm long, 8 mm wide.

*Receptacle*.—Texture: Smooth. Size: 5 mm in height, 6 mm wide. Color: Yellow-Green Group 144A. Shape: Funnel.

*Pedicel*.—Surface: Smooth. Length: 31 mm. Diameter: mm on average. Color: Yellow-Green Group 144A. Strength: Strong.

Flower bud development: Flower buds are borne singly.

Flower bloom:

*Fragrance*.—Light floral scent.

*Duration*.—The blooms have a duration on the plant of approximately 21 days. Petals fall cleanly away from plant after flowers have fully matured.

*Size*.—Flower diameter is 65 mm when open. Flower depth is 37 mm.

*Flower shape*.—Pompon, small and rounded very double flowers filled with masses of tiny petals.

*Shape of flower, side view*.—The upper portion is convex. The lower portion is concave.

Petalage: Under normal conditions, flowers have about 65 petals.

General tonality of flower: Open flowers are Red-Purple Group 62B.

Petal color:

*Upon opening, outer petals*.—Upper surface: Red-Purple Group 62C. At the basal zone, White Group 155B, with streaks of White Group 155B in the middle zone. Lower surface: Red-Purple Group 62B with streaks of White Group 155B.

*Upon opening, inner petals*.—Upper surface: Red-Purple Group 62C. At the basal zone, White Group 155B, with streaks of White Group 155B in the middle zone. Lower surface: Red-Purple Group 62B with streaks of White Group 155B.

*After opening, outer petals*.—Upper surface: Red-Purple Group 62C. At the basal zone, White Group 155B, with streaks of White Group 155B in the middle zone. Lower surface: Red-Purple Group 62B with streaks of White Group 155B.

*After opening, inner petals*.—Upper surface: Red-Purple Group 62C. At the basal zone, White Group 155B, with streaks of White Group 155B in the middle zone. Lower surface: Red-Purple Group 62B with streaks of White Group 155B.

Petals:

*Petal reflex*.—Strong.

*Margin*.—Entire and uniform. Moderate undulations.

*Shape*.—Broad and elliptic. Apex shape: Rounded. Base shape: Acute.

*Size*.—40 mm (l)×31 mm (w).

*Texture*.—Smooth.

*Thickness*.—Average.

Petaloids:

*Size*.—11 mm (l) by 11 mm (w).

*Quantity*.—About 15.

*Shape*.—Elliptical with an acute base and rounded apex.

*Color*.—The upper surface is Red-Purple Group 62C. The lower surface is Red-Purple Group 62B. At the basal zone on both sides White Group 155B.

Reproductive flower parts:

*Pollen*.—None observed.

*Anthers*.—Size: 2 mm in length. Color: Greyed-Orange Group 163B. Quantity: 38 on average.

*Filaments*.—Color: Yellow Group 8B. Length: 6 mm.

*Pistils*.—Length: 11 mm. Quantity: 25 on average.

*Stigmas*.—Color: Orange-White Group 159A.

*Styles*.—Color: Red Group 53B.

*Location of stigmas*.—Inferior in location relative to the length of the filaments and the height of the anthers.

*Hips*.—None Observed.

PLANT

*Plant growth*.—Upright and compact. Plants are 38 cm in height, and 37 cm wide.

Stems:

*Color of juvenile growth*.—Yellow-Green Group 144B.

*Color of mature growth*.—Yellow-Green Group 144A.

*Length*.—Canes are about 20 cm from the base of the plant to the flowering portion.

*Diameter*.—About 4 mm.

*Internodes*.—On mature canes about 30 mm between nodes.

*Surface texture*.—Young wood: Smooth. Older wood: Smooth.

Long prickles:

*Incidence*.—8 prickles per 10 cm of stem.

*Size*.—Average length of prickles on mature stems is 6 mm.

*Shape*.—Upper portion is linear. Lower portion is concave.

*Color*.—Juvenile prickles: Greyed-Yellow Group 162D with intonations of Greyed-Orange Group 170C. Mature prickles: Greyed-Yellow Group 162D.

Plant foliage:

*Compound leaf*.—125 mm (l)×100 mm (w).

*Quantity*.—3 leaves per 10 cm of stem on average.

*Leaf bearing angle to the stem*.—45 degrees.

*Color of juvenile foliage*.—Upper side: Yellow-Green Group 147A with marginal intonations of Greyed-Purple Group 183A. Lower side: Yellow-Green Group 147C with intonations of Greyed-Purple Group 183D shaded.

*Color of mature foliage*.—Upper side: Yellow-Green Group 146A. Lower side: Yellow-Green Group 147B.

Plant leaves and leaflets:

*Stipules*.—Size: 9 mm long, 4 mm wide. Quantity: 2 per compound leaf. Shape: Linear, slightly broad based with outward extending apices. Margins: Finely serrated. Color:

*Petiole*.—Length: 20 mm. Diameter: 2 mm. Upper surface color: Yellow-Green Group 144B with intonations of Greyed-Red Group 180C. Lower surface color: Yellow-Green Group 144A.

*Rachis*.—Length: About 35 mm. Upper surface color: Yellow-Green Group 144A with intonations of Greyed-Red Group 180A. Lower surface color: Yellow-Green Group 144A.

*Leaflet*.—Quantity: Normally 5 to 7 leaflets. Margins: Serrated. Size: Terminal leaflets are about 66 mm long, 36 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar118', substantially as illustrated and described herein, due to its abundant pink flowers, disease resistance, and extended period of bloom.

* * * * *

'Poulpar118'

'Poulpar118'

'Poulpar118'